(12) United States Patent
Arni

(10) Patent No.: US 7,987,854 B2
(45) Date of Patent: Aug. 2, 2011

(54) MANDIBULAR PROTRUSION DEVICE

(76) Inventor: Pierre Arni, Petit-Lancy (CH)

( * ) Notice: Subject to any disclaimer, the term of this patent is extended or adjusted under 35 U.S.C. 154(b) by 945 days.

(21) Appl. No.: 11/919,548

(22) PCT Filed: Apr. 13, 2006

(86) PCT No.: PCT/IB2006/001077
§ 371 (c)(1),
(2), (4) Date: Oct. 30, 2007

(87) PCT Pub. No.: WO2006/120518
PCT Pub. Date: Nov. 16, 2006

(65) Prior Publication Data
US 2010/0006107 A1 Jan. 14, 2010

(30) Foreign Application Priority Data
May 6, 2005 (EP) ..................................... 05009874

(51) Int. Cl.
*A61F 5/56* (2006.01)
*A61C 5/14* (2006.01)
*A61C 3/00* (2006.01)
(52) U.S. Cl. .............. 128/848; 128/861; 433/6; 433/19; 433/24
(58) Field of Classification Search .................. 602/902; 433/19, 24, 6, 18, 20, 21
See application file for complete search history.

(56) References Cited

U.S. PATENT DOCUMENTS

| 5,378,147 | A | 1/1995 | Mihailowitsch et al. |
| 6,012,920 | A | 1/2000 | Woo et al. |
| 7,146,982 | B2 | 12/2006 | Mousselon et al. |

FOREIGN PATENT DOCUMENTS

| DE | 295 06 512 U1 | 6/1995 |
| EP | 1 459 699 A1 | 9/2004 |
| FR | 2 816 203 A | 5/2002 |
| FR | 2 831 427 A | 5/2003 |

*Primary Examiner* — Patricia M Bianco
*Assistant Examiner* — Victoria Hicks
(74) *Attorney, Agent, or Firm* — Young & Thompson

(57) ABSTRACT

A mandibular protrusion device includes an upper dental tray to be placed on the upper dental arch of a patient and a lower dental tray to be placed on the lower dental arch, as well as two lateral links for connecting both trays in order to advance or draw back the lower dental arch during a vertical movement between both dental arches, each lateral link including an element of traction attached to the trays via its ends. Each lateral link includes ball pivots having an opening for receiving an end of an element of traction, and each tray includes two lateral seats for accommodating a ball pivot connected to an element of traction so that the lateral links are connected to the trays via a ball pivot joint. A corresponding lateral link and a method for assembling the mandibular protrusion device are also disclosed.

12 Claims, 3 Drawing Sheets

MANDIBULAR PROTRUSION DEVICE

Object of the present invention is a mandibular protrusion device comprising an upper dental tray to be placed onto the upper dental arch of a patient, and a lower dental tray to be placed onto the lower dental arch, as well as two lateral links for linking the two trays so as to advance the lower dental arch during a vertical movement between the two dental arches, each lateral link comprising a means of traction attached via its ends to the trays.

This kind of dental appliance that is used against the snoring or sleep apnea is generally known in the field of dentofacial orthopedics as a protrusion appliance. Other types of appliances exist that are used in this context, but for what follows, only the intraoral devices and specifically those of the type mentioned above are important. As to snoring, more particularly, this phenomenon normally is caused by weak neck muscle tonus during sleep. The respiratory passages thus are constricted or, in apnea, even obturated. Air circulation in the constricted respiratory passages will then occur at a higher speed than is normal, and generates noise by setting in motion the relaxed structures in the neck. For this reason the phenomenon is more frequent among old people the muscles of whom tend to lose tonus with age.

The appliances of this kind tend to reestablish a normal air circulation and above all one having a normal speed, by attempting to widen the respiratory passages. To this end they generally hold the lower jaw forward so as to open the pharyngeal segment of the respiratory passages, which is done via lateral links having an adequate length, and connecting the upper and lower dental trays commonly placed onto the upper and lower dental arches during the night.

The lateral links of known appliances more particularly are subject to traction during a vertical movement between the upper and lower jaws, that is, when breathing occurs via the open mouth. Therefore, the links normally are made of a flexible material but admit no longitudinal stretching of the links. Thus, by letting the longitudinal axis of the links that are mounted on the outside of the trays, be oriented in a direction from bottom back of the lower jaw to top front of the upper jaw, an opening of the mouth that is caused by a dropping of the lower jaw in sleep will produce a forward protrusion of the lower jaw and a corresponding opening of the respiratory passages. The lower jaw, and with it the base of the tongue, will then be held or protruded forward so as to help keeping the pharyngeal segment of the respiratory passages sufficiently wide open to establish or favor a normal respiration without snoring or, in certain cases, so as to reduce sleep apneas.

Conventionally, the lateral links are fixed on the trays by snap fit, for instance, which has several drawbacks. First, the snap fitting occurs on the outside of a tray where the link should be mounted. The cheek of the patient and the inside of his mouth will then be directly exposed to the link's end or maybe to an additional part needed to produce the snap fit, which may cause a feeling of discomfort, or friction and even injury, depending on the size and shape of said parts, which may lead the patient to practically no longer use the appliance. In terms of functionality of the device, snap fit is not an ideal solution inasmuch as it is desirable that the links have a certain lateral and rotary mobility in order to secure a corresponding mobility laterally and vertically in particular, between the upper and lower jaws. This articulation should at the same time be strong enough so as to avoid breaking. If the links are mounted in a definite way by snap fit, the user moreover will then be deprived of the possibility to adapt the lengths of the lateral links by himself, by changing them. Snap fitting will in this case also complicate manufacture of such a device, and entail the corresponding expenses for the manufacturer.

It is the aim of the present invention to remedy said drawbacks, and more particularly propose a device that will allow the inside of the patient's mouth to be protected, while at the same time providing a less fragile articulation and improved mobility of the ends of the links, as well as facilitating the manufacture and use of the device, in particular so as to let the user himself change the links.

To this end, the invention is characterized by the characteristics listed in claims 1, 10, and 11.

A device according to the present invention notably comprises lateral links having ball pivots with an opening apt to receive one end of a means of traction of the link, while each tray of the device comprises two lateral seats apt to accommodate a ball pivot connected with a means of traction. Thus, the lateral links are connected with the trays via a ball-and-socket joint. Moreover, the ends of the links are found inside lateral seats that have a smooth outside surface, and for this reason constitute a protection for the patient's mouth. It should also be noted that size is an important factor for this kind of device, and that such a link is particularly apt to be miniaturized, thus reducing the bulkiness of said dental appliance and yielding higher comfort for the patient.

A lateral link that is intended to be incorporated into such a mandibular protrusion device may more particularly be manufactured independently of said device, and is distinguished by the fact that the ends of the means of traction of the link are apt to be accommodated detachably in an opening of the ball pivot of the lateral link, this ball pivot that is connected with a means of traction being apt to be accommodated detachably in a lateral seat of a tray in such a way that the lateral link may be connected with the trays in a detachable way via a ball-and-socket joint.

Assembly of such a mandibular protrusion device comprises the steps of sliding one end of a means of traction of a lateral link through a hole made in the lateral seat that is positioned in the longitudinal axis of the means of traction, to fit a ball pivot of the lateral link over the end of the means of traction that passes through the hole in the lateral seat, snap fitting said ball pivot into an inner cup of the lateral seat, and repeating these steps for all the ends of the means of traction of the two lateral links of the device, in such a way that the lateral links are laterally connected with the trays via a ball-and-socket joint. The assembly and the manufacture as well as the use of the device thus are facilitated, particularly so with respect to link changes by the user. In fact, the user himself can manually perform this last-mentioned operation without any problem, since each articulation is realised by mutually fitting together three parts that are not mounted onto each other in a definite way. Such an articulation at the same time is very stable with respect to breaking, since the end of a link is accommodated in a mobile fashion within the cups of the trays, and since the force of traction acting on the links is applied against the walls of these cups, rather than against fragile parts that are used for a snap fit as in the prior art.

Further advantages will become apparent from the characteristics expressed in the dependent claims, as well as from the description which hereinafter will present the invention in greater detail with the aid of drawings.

The attached drawings represent one embodiment of the invention as an example.

FIG. 1a is a schematic perspective view of a device according to the present invention that shows a lateral link mounted on dental trays.

FIG. 1b schematically illustrates a horizontal section through the device of FIG. 1a at the level of the lateral seats where a ball pivot connected with the end of a means of traction of a lateral link is accommodated.

FIG. 2b shows a lateral view of the parts of FIG. 2a.

FIG. 2c is a bottom view of the assembled parts of FIG. 2a.

The invention will now be described in detail while referring to the attached drawings illustrating one embodiment of the invention as an example.

Figure 1A:
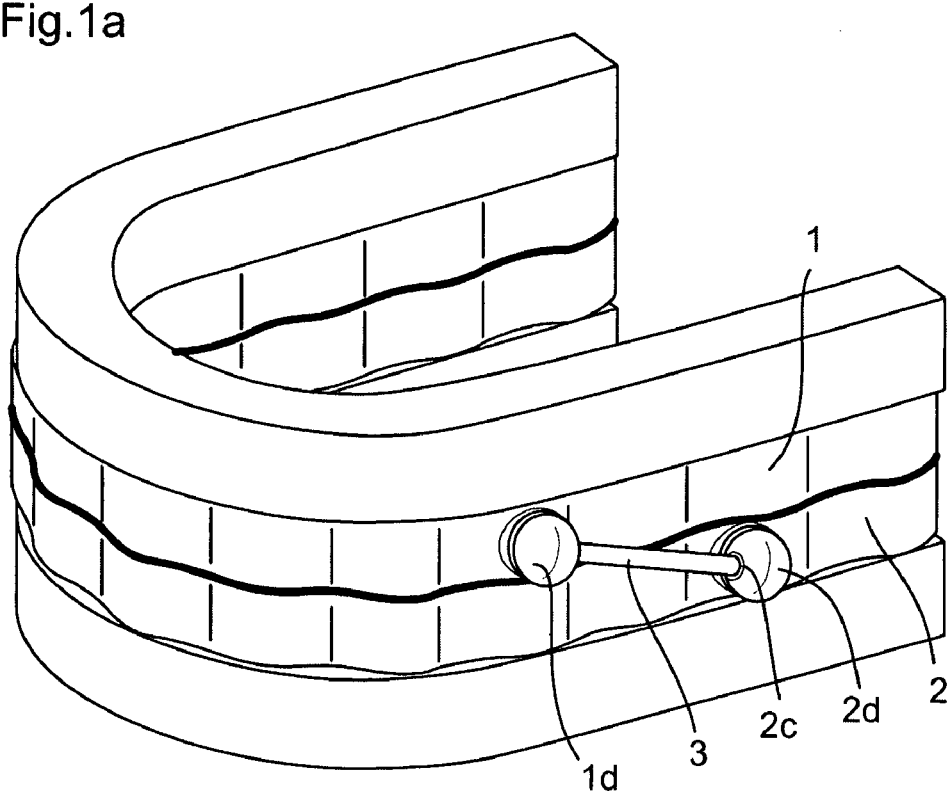
FIG. 1c represents a partial view of FIG. 1b that shows in detail a lateral seat with a ball pivot connected with an end of a means of traction of a lateral link.

Referring to FIG. 1a, the important components of a mandibular protrusion device according to the present invention are clearly visible. They comprise an upper dental tray 1 to be placed onto the upper dental arch of a patient, and a lower dental tray 2 to be placed onto the lower dental arch. The two dental trays 1 and 2 normally are manufactured by thermoforming while for instance using a cast of the patient's teeth in order to exactly reproduce the individual profile of the corresponding dental arch to which they may then be fixed by snap fitting, above all during the night. Preferably, the dental trays are made of a thermoformable transparent plastic material, such as that known under the trade names of Duran or Essix, but they may also be manufactured by a process other than thermoforming, as well as from any other suitable material. The conventional manufacturing modes of these trays may actually be used as well for the devices according to the present invention, with an additional step that will be described in detail later in the text.

Figure 2A:
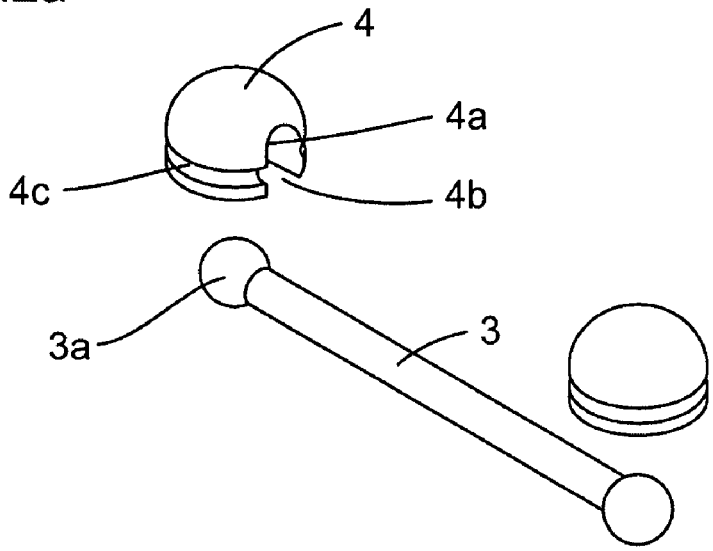
FIG. 2a is a perspective view of a lateral link with a means of traction and corresponding ball pivots.
Figure 2B:
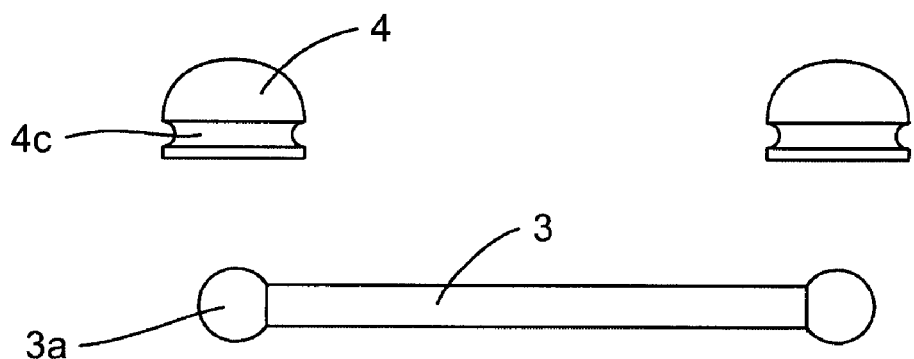
Figure 2C:
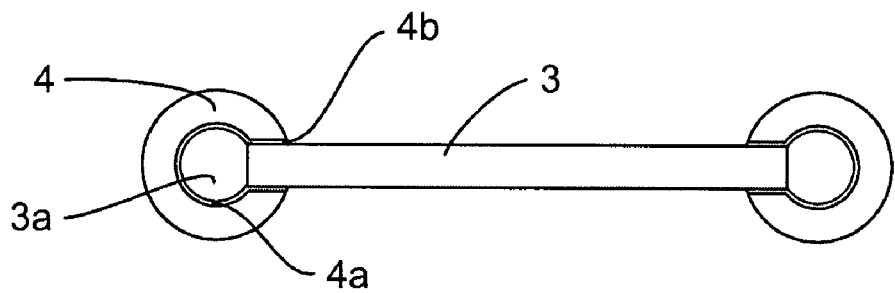

The device also comprises two lateral links apt to link the two trays 1, 2 so as to move the lower dental arch forward during a vertical movement between the two dental arches. As illustrated in FIGS. 2a to 2c, each lateral link comprises to this end a means of traction 3 to be attached with its ends 3a to the trays 1, 2. The links are mounted on the outer sides of the trays 1, 2 in such a way that their longitudinal axes run in a direction from the bottom back of the lower jaw to the top front of the upper jaw when the device has been placed, which is as shown in FIG. 1a.

As mentioned in the introduction, the lateral links undergo traction during a vertical movement between the upper and lower jaws. It follows that normally they are manufactured from a flexible material, though one that does not admit a stretching in the longitudinal axis of the links, preferably also of plastic, e.g., of polyoxymethylene (POM) that is a material often used in this field, or of a metal such as titanium. This holds true in particular for the means of traction 3 of a lateral link that corresponds to a link's intermediate segment between its ends 3a, and may for instance consist of a connecting rod or cord.

The ends 3a of the means of traction 3 of a lateral link are preferably spherical, but they could equally well be of some other equivalent shape, e.g., hemispherical. Preferably, the means of traction 3 and the spherical ends 3a of a lateral link are made as a single integrated part, notably in the embodiment having a connecting rod, rather than being joined together after their manufacture. This attachment part is available in several lengths, so that one may regulate the protrusion of the lower jaw, as will become more clearly apparent in what follows.

Figure 1B:
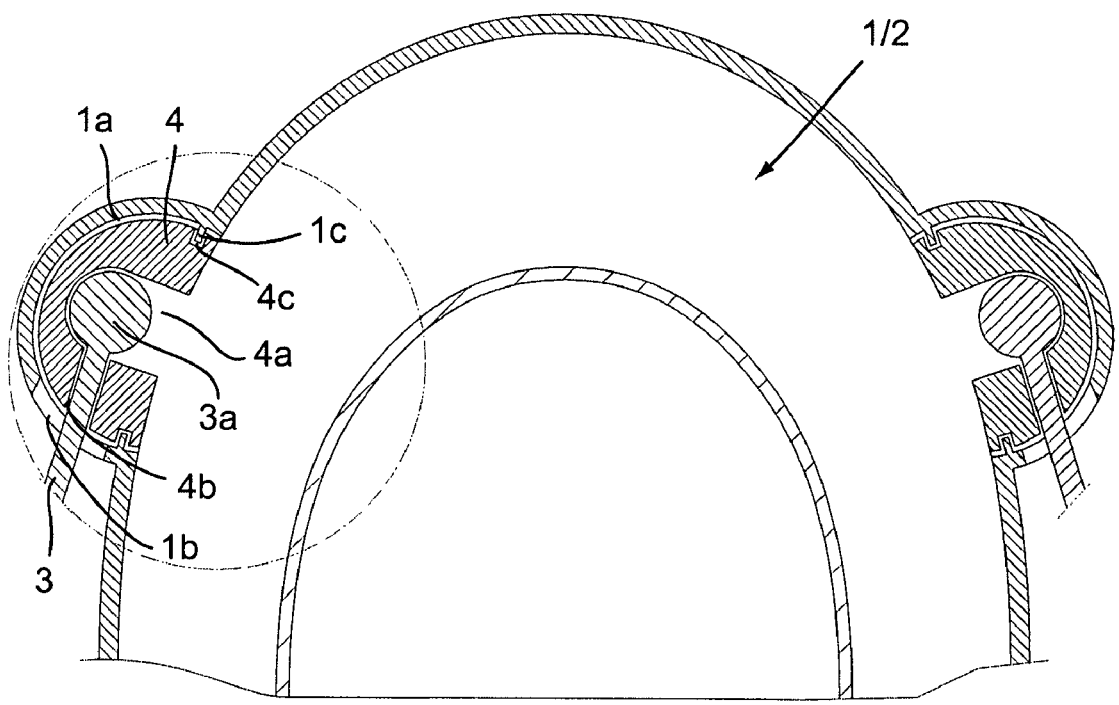
Figure 1C:
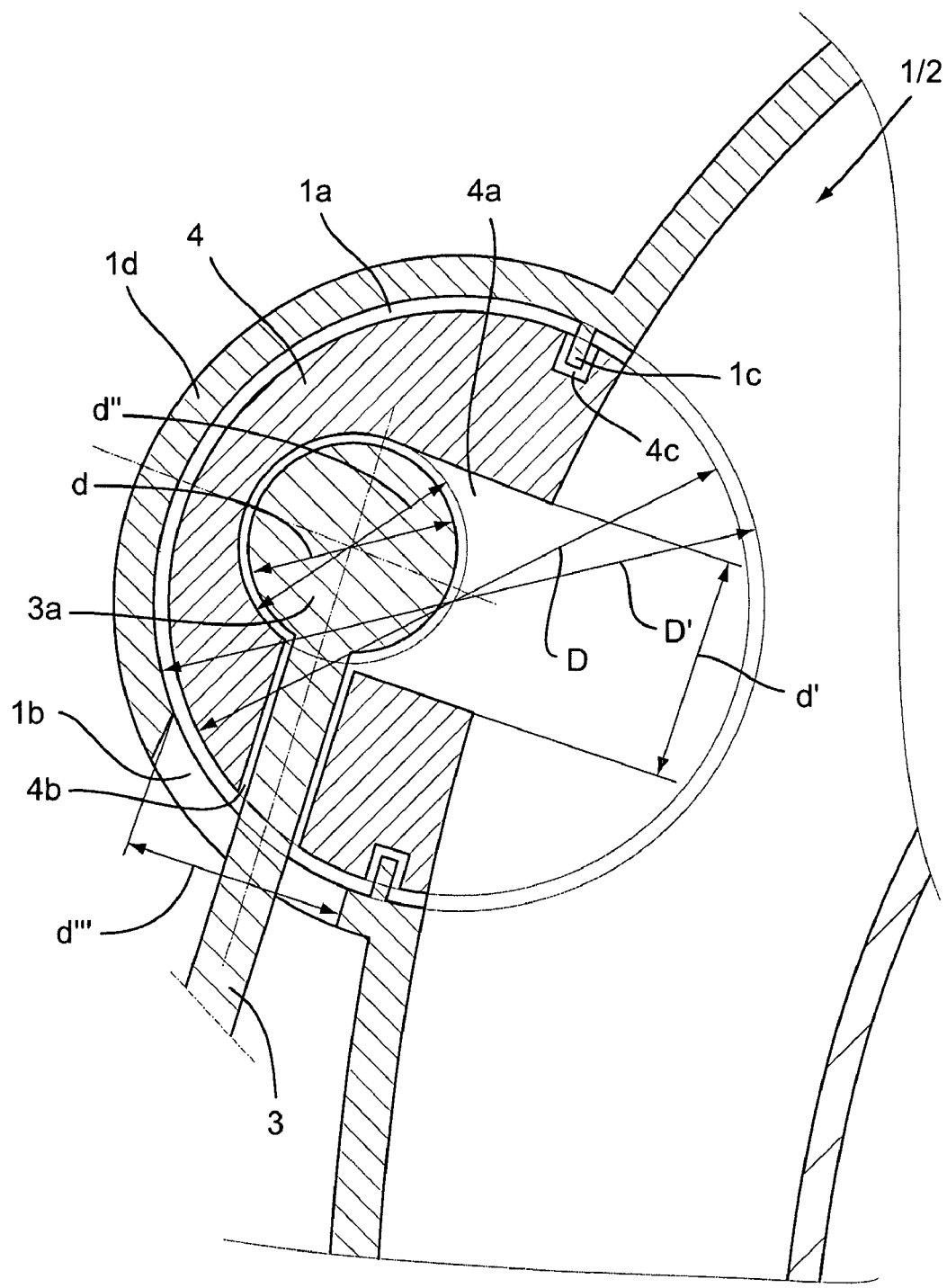

In addition, the lateral links of a device according to the present invention notably comprise ball pivots 4 that are also well illustrated in FIGS. 2a to 2c. These ball pivots 4 may consist of the same material as the means of traction, and each has one opening 4a, 4b apt to receive one end 3a of a means of traction 3 of the link in order to connect the means of traction 3 at each of its ends 3a to a ball pivot 4. Simultaneously, each tray 1, 2 comprises two lateral seats 1d, 2d apt to accommodate a ball pivot 4 connected with a means of traction 3, as schematically shown in FIGS. 1b and 1c. The lateral links thus may be detachably connected with the trays 1, 2 via a ball-and-socket joint.

This general design concept enables an opening of the mouth that is caused by a dropping of the lower jaw during sleep, to give rise to a forward protrusion of the lower jaw and a corresponding opening of the pharyngeal respiratory passages.

The lateral seats 1d, 2d of a tray 1, 2 are situated on its outer side, and comprise a hole 1b, 2b that serves to define the direction of the longitudinal axis of the means of traction 3 that is accommodated there. They also comprise an inner cup 1a, 2a of substantially hemispherical shape, where the substantially circular entrance of this inner cup 1a, 2a will be adjoining the corresponding dental arch once the device has been placed onto the dental arches, as represented in FIGS. 1b and 1c.

For manufacture of trays 1, 2 with these lateral seats 1d, 2d, one merely needs—as indicated hereinabove—to place at the positions specified for the articulations of the lateral links, for instance a negative of a ball pivot 4 made of POM or of a disintegrating material, onto a replica of the patient's dental arch that has been obtained with the aid of an individual cast. Subsequently the trays are thermoformed in conventional manner, but with the negatives in their place, and each of the negatives may be lifted from the lateral seats 1d, 2d thus formed when the trays 1, 2 have cooled down. At the end, the lateral seats 1d, 2d may be touched up by milling, for instance, in order to improve the shape of the inner cups 1a, 2a while the holes 1b, 2b may be cut out at the desired positions in order to define the direction of the longitudinal axis of the means of traction 3 that is accommodated in the corresponding inner cup 1a, 2a.

The ball pivots 4 of a lateral link have an substantially hemispherical shape and an outer diameter D slightly smaller than the inner diameter D' of the inner cups 1a, 2a of the lateral seats 1d, 2d in the dental trays 1, 2 so that they may be accommodated in these trays.

As indicated in FIG. 1c, each ball pivot 4 moreover comprises an annular groove 4c around its outside wall that circles the opening of a cavity 4a that will be described in detail hereinafter, the groove being situated approximately at the level of the plane of the hemispherical shape of ball pivot 4. The inner cups 1a, 2a of a tray 1, 2 that accommodate the ball pivot 4 have an annular tongue 1c, 2c apt to snap fit into the annular groove 4c of the ball pivot 4, the tongue being located, in corresponding manner, at approximately the level of the substantially circular entrance to the inner cup 1a, 2a. This allows a rotary movement of ball pivot 4 in the plane of the annular groove 4c and annular tongue 1c, 2c. It will obviously be possible to specify the inverse arrangement, that is, an annular tongue around the outer wall of a ball pivot 4 and a groove in the inner cup 1a, 2a of a tray 1, 2. The tongue need not be annular; the rotary movement could be limited by making the groove, also only over a segment of the circumference of the ball pivot or lateral seat.

Describing the opening 4a, 4b of a ball pivot 4 in detail, this opening comprises an oblong passage 4b apt to receive an oblong segment of a means of traction 3 of the link, i.e., a segment of the connecting rod or cord, as well as a cavity 4a of substantially hemispherical shape apt to receive an end 3*a* of a means of traction 3 of the lateral link, as can be seen in FIGS. 1*c*, 2*a*, and 2*c*.

The diameter d of the spherical ends 3*a* of a means of traction 3 is slightly larger than the diameter d' of the opening of cavity 4*a* of a ball pivot 4 at the level of the substantially circular entrance of this cavity 4*a*, and slightly smaller than the inner diameter d" of cavity 4*a*. The dimensions of the oblong passage 4*b* normally correspond, substantially to the dimensions of the means of traction 3, so as to allow introduction of the means of traction into the ball pivot 4 and, once placed, a rotary movement around the longitudinal axis of the means of traction 3. This design admits an assembly of the means of traction 3 with ball pivot 4 by insertion of the end 3*a* of the means of traction 3 into cavity 4*a* of ball pivot 4. A projection could also be added at the level of the oblong passage 4*b* in order to also fit the means of traction 3.

The diameter d'" of the hole 1*b*, 2*b* of a lateral seat 1*d*, 2*d* of a tray 1, 2, finally, is larger than the diameter d of the spherical ends 3*a* of a means of traction 3 of a lateral link in order to admit assembly of the means of traction 3 with the ball pivot 4 across this hole 1*b*, 2*b*. The place of this hole 1*b*, 2*b* on a lateral seat of a tray 1, 2 is selected depending on the position of these seats on the tray, in such a way that the holes will define the direction of the longitudinal axis of the lateral link, and yield a sufficiently large mobility of the links as well as of the trays 1, 2.

The lateral seats 1*d*, 2*d* of the upper dental tray 1 are in fact located on its outer side, often at the level of the canines, and the lateral seats 1*d*, 2*d* of the lower dental tray 2 are located on its outer side at the level of the premolars. The centers of the holes 1*b*, 2*b* normally are placed into the lateral seats 1*d*, 2*d* in such a way that they will define the longitudinal axis of the means of traction 3 as a straight line between the centers of seats 1*d*, 2*d* of each side of the trays 1, 2.

For the sake of being complete, it should be noted that the positions of the lateral seats on the trays 1, 2 could be inverted, i.e., in the front on the lower jaw and in the back on the upper jaw, so as to obtain a device that is apt to pull the lower jaw backwards. This type of an appliance could evidently be designed by using the same characteristics as those described above, and might be useful in certain applications that aim at correcting a malformation in the facial bones and notably in the lower jaw.

As to the lateral link by itself, it may evidently be manufactured independently of trays 1, 2, and vice versa. As will appear from the above description, such a link is supposed to be integrated into a mandibular protrusion device that comprises an upper dental tray 1 to be placed onto the upper dental arch of a patient, and a lower dental tray 2 to be placed onto the lower dental arch. The link is apt to link the two trays 1, 2 in such a way as to move the lower dental arch forward during a vertical movement between the two dental arches, and comprises a means of traction 3 that is attached via its ends 3*a* to the trays 1, 2. The ends 3*a* of the means of traction 3 of the link are more particularly apt to be detachably accommodated in an opening 4*a*, 4*b* of a ball pivot 4 of the lateral link. This ball pivot 4 that is connected with a means of traction 3 is apt to be detachably accommodated in a lateral seat 1*d*, 2*d* of a tray 1, 2. The lateral link thus may be detachably connected with the trays 1, 2 via a ball-and-socket joint.

As to the process of assembly of a mandibular protrusion device according to the present invention, this process comprises the following steps.

At first one end 3*a* of a means of traction 3 of a lateral link is made to slide from the outer side of one tray 1, 2 through the hole 1*b*, 2*b* in a lateral seat 1*d*, 2*d* that defines the direction of the longitudinal axis of the means of traction 3 that is accommodated there, in such a way that the end 3*a* be accessible from the other side of seat 1*d*, 2*d*. Then a ball pivot 4 is fitted upon the end 3*a* of the means of traction 3 of the lateral link that had been pushed through hole 1*b*, 2*b* of a lateral seat 1*d*, 2*d*. This ball pivot 4 is then snap fitted into the inner cup 1*a*, 2*a* of the lateral seat 1*d*, 2*d* of a tray 1, 2, the articulation thus being attained at one end of the lateral link. These steps are repeated for all ends 3*a* of the means of traction 3 of the two lateral links, so that all lateral links will be laterally connected with the trays 1, 2 via a ball-and-socket joint.

It should be noted that the characteristics mentioned hereinabove, both of the device and of its assembly, allow a detachable mutual fitting of the three important components of the device according to the present invention, particularly so of (the end 3*a* of) the means of traction 3 into ball pivot 4, and of the ball pivot 4 into the lateral seat of a tray 1, 2. For this reason the device realizes—notably with the aid of ball pivot 4—in a simple and efficient way an articulation that corresponds to a ball-and-socket joint. This layout will then allow a slight lateral movement and a vertical movement, that is, the opening of the mouth, between the upper and lower jaws while guaranteeing the desired forward protrusion of the lower jaw during a vertical movement between the two. The possibility of having these movements, and the concept of a ball-and-socket joint, make the device more break-resistant. Moreover, the lateral seat in the trays on the outer side of the appliance forms a protection for the tissue of the patient's mouth facing the articulation. The lateral seat at the same time provides an enhanced safety even in the sense that in the case of a broken link there is no risk that the patient swallow a part of the system, since other than in snap-fit fastening, the ends of the lateral links always remain accommodated inside the trays, and hence cannot separate from the appliance. On account of the detachable fitting, even the user may readily change the lateral links or the connecting rods, and thus easily regulate the forward movement of the lower jaw, by selecting a connecting rod of adequate length. At the same time this simplifies, not only the use but equally well the manufacture of the device. These advantages of the device according to the present invention are obtained while retaining the manufacturing modes for this kind of product as well as its price, chiefly owing to the advantageous design concept of the lateral link.

The invention claimed is:

1. Mandibular protrusion device comprising an upper dental tray (1) to be placed onto the upper dental arch of a patient, and a lower dental tray (2) to be placed onto the lower dental arch, as well as two lateral links apt to link the two trays (1, 2) so as to advance or retract the lower dental arch during a vertical movement between the two dental arches, each lateral link comprising a means of traction (3) attached via its ends (3*a*) to the trays (1, 2), characterized in that each lateral link comprises ball pivots (4) having an opening (4*a*, 4*b*) apt to receive one end (3*a*) of a means of traction (3), and in that each tray (1, 2) comprises two lateral seats (1*d*, 2*d*) apt to accommodate one ball pivot (4) connected with a means of traction (3), in such a way that the lateral links may be connected with the trays (1, 2) via a ball-and-socket joint.

2. Device according to claim 1, characterized in that each lateral seat (1*d*, 2*d*) of a tray (1, 2) is located on its outer side, and comprises a hole (1*b*, 2*b*) defining the direction of the longitudinal axis of the means of traction (3) that is accommodated there, as well as an inner cup (1*a*, 2*a*) of substantially hemispherical shape, the substantially circular entrance of said inner cup (1*a*, 2*a*) adjoining the dental arch when the device has been placed.

3. Device according to claim 2, characterized in that each ball pivot (4) has a substantially hemispherical shape, and the opening (4a, 4b) of a ball pivot (4) comprises an oblong passage (4b) apt to receive an oblong segment of a means of traction (3), and a cavity (4a) of substantially hemispherical shape apt to receive one end (3a) of a means of traction (3).

4. Device according to claim 3, characterized in that each ball pivot (4) comprises an annular groove (4c) around its outside wall that circles the opening of the cavity (4a), the inner cup (1a, 2a) of a tray (1, 2) that accommodates the ball pivot (4) being provided with an annular tongue (1c, 2c) apt to snap fit into the annular groove (4c) of ball pivot (4) so as to allow a rotary movement of ball pivot (4) in the plane of the annular groove (4c) and annular tongue (1c, 2c).

5. Device according to claim 2, characterized in that each ball pivot (4) comprises an annular groove (4c) around its outside wall that circles the opening of the cavity (4a), the inner cup (1a, 2a) of a tray (1, 2) that accommodates the ball pivot (4) being provided with an annular tongue (1c, 2c) apt to snap fit into the annular groove (4c) of ball pivot (4) so as to allow a rotary movement of ball pivot (4) in the plane of the annular groove (4c) and annular tongue (1c, 2c).

6. Device according to claim 1, characterized in that the ends (3a) of a means of traction (3) are spherical.

7. Device according to claim 6, characterized in that the diameter (d) of the spherical ends (3a) of a means of traction (3) is larger than the diameter (d') of the opening of cavity (4a) of a ball pivot (4) at the level of the substantially circular entrance of this cavity (4a), and smaller than the inner diameter (d") of the cavity (4a), so as to allow a snap-fit assembly of the means of traction (3) with the ball pivot (4).

8. Device according to claim 7, wherein each lateral seat (1d, 2d) of a tray (1, 2) is located on its outer side, and comprises a hole (1b, 2b) defining the direction of the longitudinal axis of the means of traction (3) that is accommodated there, as well as an inner cup (1a, 2a) of substantially hemispherical shape, the substantially circular entrance of said inner cup (1a, 2a) adjoining the dental arch when the device has been placed, and the diameter (d''') of the hole (1b, 2b) of a lateral seat (1d, 2d) of a tray (1, 2) is larger than the diameter (d) of the spherical ends (3a) of a means of traction (3), so as to allow an assembly of the means of traction (3) with the ball pivot (4) across this hole (1b, 2b).

9. Device according to claim 1, characterized in that each ball pivot (4) has a substantially hemispherical shape, and the opening (4a, 4b) of a ball pivot (4) comprises an oblong passage (4b) apt to receive an oblong segment of a means of traction (3), and a cavity (4a) of substantially hemispherical shape apt to receive one end (3a) of a means of traction (3).

10. Device according to claim 9, characterized in that each ball pivot (4) comprises an annular groove (4c) around its outside wall that circles the opening of the cavity (4a), the inner cup (1a, 2a) of a tray (1, 2) that accommodates the ball pivot (4) being provided with an annular tongue (1c, 2c) apt to snap fit into the annular groove (4c) of ball pivot (4) so as to allow a rotary movement of ball pivot (4) in the plane of the annular groove (4c) and annular tongue (1c, 2c).

11. Device according to claim 1, characterized in that the lateral seats (1d, 2d) of the upper dental tray (1) are located on its outer side at the level of the canines, and the lateral seats (1d, 2d) of the lower dental tray (2) are located on its outer side at the level of the premolars, while the centers of the holes (1b, 2b) in the lateral seats (1d, 2d) are positioned so as to define the direction of the longitudinal axis of the means of traction (3) in a straight line between the centers of the seats (1d, 2d) on each side of the trays (1, 2).

12. Device according to claim 1, characterized in that a means of traction (3) consists of a connecting rod having spherical ends (3a), and is integrally made as a single part.

* * * * *